United States Patent
Stürzebecher

(10) Patent No.: US 7,035,745 B2
(45) Date of Patent: Apr. 25, 2006

(54) STATISTICAL TEST METHOD FOR OBJECTIVE VERIFICATION OF AUDITORY STEADY-STATE RESPONSES (ASSR) IN THE FREQUENCY DOMAIN

(75) Inventor: Ekkehard Stürzebecher, Petershagen (DE)

(73) Assignee: Oticon A/S, Smørum (DK)

( * ) Notice: Subject to any disclaimer, the term of this patent is extended or adjusted under 35 U.S.C. 154(b) by 0 days.

(21) Appl. No.: 10/793,742

(22) Filed: Mar. 8, 2004

(65) Prior Publication Data

US 2005/0021264 A1    Jan. 27, 2005

Related U.S. Application Data

(63) Continuation-in-part of application No. 10/772,423, filed on Feb. 6, 2004, now abandoned.

(30) Foreign Application Priority Data

Feb. 7, 2003    (EP)    ................... 03388010

(51) Int. Cl.
*G06F 19/00*    (2006.01)
(52) U.S. Cl. ............... 702/77; 600/559; 381/60
(58) Field of Classification Search ........ 702/66, 702/67, 75–77, 108, 109, 189; 600/559; 381/60; 73/585
See application file for complete search history.

(56) References Cited

U.S. PATENT DOCUMENTS

| | | | |
|---|---|---|---|
| 6,071,246 A * | 6/2000 | Sturzebecher et al. | 600/559 |
| 2004/0116825 A1 * | 6/2004 | Sturzebecher | 600/559 |
| 2005/0143951 A1 * | 6/2005 | Sturzebecher | 702/179 |

FOREIGN PATENT DOCUMENTS

WO    02098291    12/2002

OTHER PUBLICATIONS

Sturzebecher et al; 2002; www.beraphone.com/english/Beraphon/ARTIKEL/Hessen_2002e.pdf ; 14 pages.*
E. Stürzebecher et al., "Objective Response Detection in the Frequency Domain: Comparison of Several q-Sample Tests" in Audiology & Neoro-Otology, BD 4, Nr. 1, Jan. 1999, pp. 2-11 (XP 009013652).

* cited by examiner

*Primary Examiner*—Patrick J. Assouad
(74) *Attorney, Agent, or Firm*—Dykema Gossett PLLC

(57) ABSTRACT

The invention relates to statistical testing method for the objective verification of auditory steady-state responses (ASSR) in the frequency domain by using a "q-sample uniform scores test" whereby only the phase angles are used. Phase angles computed by Fourier transformation are used in one embodiment example. In another embodiment example, spectral amplitudes and phase angles are used; however, the phase angles remain unranked while ranks for the spectral amplitudes are still taken into account for the test. In yet another embodiment example, the values of the phase angles and of the spectral amplitudes are used directly (unranked) whereby said values are computed by means of Fourier transformation. The invention relates also to a testing device to carry out the statistical test method.

1 Claim, 2 Drawing Sheets

Figure 1:
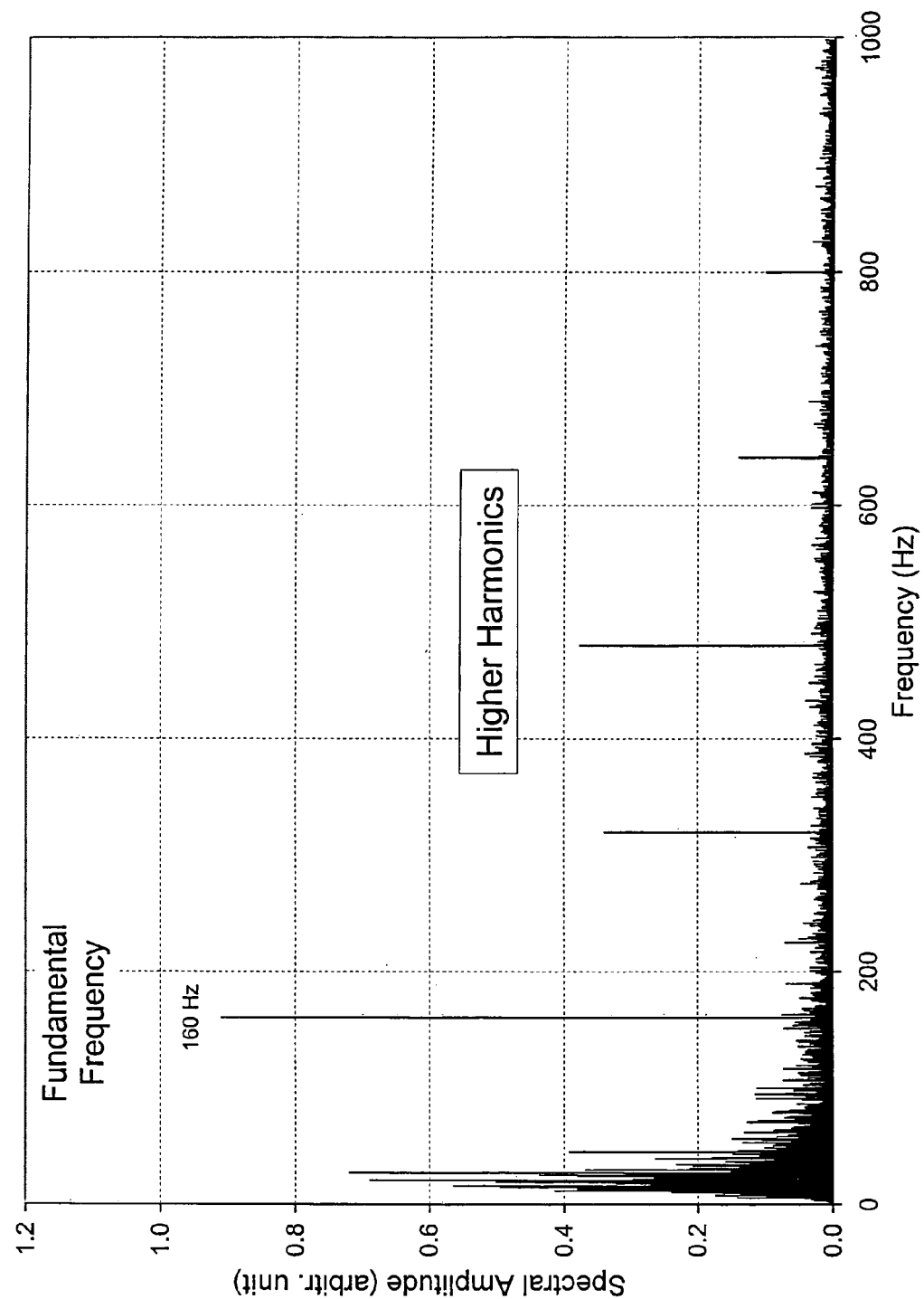

STATISTICAL TEST METHOD FOR OBJECTIVE VERIFICATION OF AUDITORY STEADY-STATE RESPONSES (ASSR) IN THE FREQUENCY DOMAIN

This application is a continuation-in-part of application Ser. No. 10/772,423, filed Feb. 6, 2004 now abandoned.

The invention relates to the field of objective measuring of hearing ability by using evoked auditory steady-state responses (ASSR). The proposed methods for objective verification of ASSR in the frequency domain can be employed in an ASSR-based hearing screening of a newborn as well as in objective audible threshold measuring based on ASSR.

There are two different types of ASSR known:
1. Click-evoked ASSR
2. ASSR evoked through a continuous amplitude or frequency-modulated tone, which are also referred to as amplitude-modulation following response (AMFR).

Both types of ASSR are described (FIG. 1) in the frequency domain by so-called harmonics (one fundamental wave and several harmonic waves). The frequency of the fundamental wave corresponds to the click stimulus rate or the frequency of the modulation signal. The frequencies of the harmonic waves are multiples of the frequency of the fundamental wave. This means that the entire response is represented by a few spectral lines. The substantial portion of the noise power caused by the asynchronous electroencephalogram (asynchronous EEG) is concentrated, in contrast, on the spectral lines lying between the harmonics.

The objective verification of the ASSR occurs almost exclusively in the frequency domain. Each spectral line in the frequency domain is defined by a spectral amplitude and a phase angle. Several statistical methods are known for response verification in the spectral domain, which interpret in so-called one-sample tests only the phase angle or also the phase together with the amplitude of an individual spectral line, preferably the first harmonic (fundamental wave) (Stapells D R, Makeig S, Galambos R. Auditory steady-state responses: Threshold prediction using phase coherence. Electroencephalography and Clinical Neurophysiology 1987;67:260–270; Valdes J L, Perez-Abalo M C, Martin V, Savio G, Sierra C, Rodriguez E, Lins O. Comparison of statistical indicators for the automatic detection of 80 Hz auditory steady state response (AMFR). Ear and Hearing 1997;18:420–429). The recorded time signal is transformed by epochs into the frequency domain for this purpose. The length of the transformed epochs must be selected in such a manner that the epoch is an exact integral multiple of the length of the period of the click stimulus rate or of the modulation frequency. The spectral line (fundamental frequency) corresponding to the click stimulus rate or the modulation frequency is searched and tested in the frequency spectrum that exists after the transformation. The advantage of the response verification in the frequency domain, compared to the direct verification in the time domain, is that the portion of the noise power in the spectral domain (represented by the spectral lines lying between the harmonics) does not interfere with the response detection since these spectral lines are not included in the testing. The disadvantage of the so-called "one-sample tests" employed in the above-mentioned publication exists in the limitation of the statistical testing on the fundamental frequency. However, ASSR are not represented, in the rule, alone by the click-repetition frequency or the fundamental frequency corresponding to the modulation frequency, but they are also represented by one or several harmonic waves for which there is allotted a portion of the response signal power, which is not be ignored. An objective verification method limited only to the fundamental wave is therefore not optimal.

Statistical testing methods working in the frequency domain are also described by Stürzebecher and Stürzebecher et al. (Stürzebecher E: "Method for hearing screening of newborn by means of steady-state response evoked with high click rate", European patent application EP 01610060.4.; Stürzebecher, E, Cebulla M, Baag M, Thie R: "Verfahren zur objektiven frequenzspezifischen Hörschwellenbestimmung mittels der Amplitude-Modulation Following Response (AMFR)", European patent application EP1099408 A2). So-called q-sample test are employed as statistical tests, which include the fundamental wave as well as the relevant harmonic waves for the statistical verification of the ASSR. We are dealing thereby with the "q-sample uniform scores test" known in the literature (Mardia K V. Statistics and directional data. Academic Press London and New York 1972) and a modification of this test proposed by Stürzebecher et al. (Stürzebecher, E, Cebulla M, Baag M, Thie R: "Verfahren zur objektiven frequenzspezifischen Hörschwellenbestimmung mittels der Amplitude-Modulation Following Response (AMFR)", European patent application EP1099408 A2).

The calculation rule for the "q-sample uniform scores test" described my Mardia, 1972, is:

Let $\{x_{ik}; 1 \leq i \leq m, 1 \leq k \leq q\}$ be a collection of random variables (phase angles $\phi_{ik}$); q is the number of samples (spectral lines) with the sample size m (number of epochs), i.e. there are q×m=n phase angle values. The n phase values were ranked in a single sequence. Let $r_{ik}$, i=1, . . . , m, be the ranks of the phase angles in the kth sample.

The phase angles $\phi_{ik}$ are then replaced by the uniform scores $$\beta_{ik} = \frac{2 \cdot \pi \cdot r_{ik}}{n}.$$

The test statistics used is $$W = \frac{2}{m} \cdot \sum_{k=1}^{q} (C_k^2 + S_k^2) \text{ with}$$

$$C_k = \sum_{i=1}^{m} \cos\beta_{ik};$$

$$S_k = \sum_{i=1}^{m} \sin\beta_{ik}$$

where
$r_{ik}$ are the ranks of the n phase angles (n=q×m), q is the number of samples (number of included spectral lines) and m is the sample size (number of epochs).
W is distributed as Chi-square with 2 (q−1) degrees of freedom.

As it can be seen from the calculation rule, only phase angles are used and the spectral amplitudes are not considered. Another loss of information is added: only ranks of phase angles are used in the calculation of the test value and not the phase angles themselves. This has, nevertheless, the advantage that the method is nonparametric; however, the result of the information loss taken in exchange is a lower test power. However, the test power should be as high as possible for hearing screening and for the objective audible threshold determination. Stürzebecher et al. have therefore devised a modification of the test (referred here as Test Modification 1), which considers also the spectral amplitudes in the form of ranks of amplitudes in addition to the phases:

TEST MODIFICATION 1

Additionally to the phase angles, the spectral amplitudes $A_{ik}$ were taken into account. Like the phase angles, the spectral amplitudes $A_{ik}$ are ranked in a single sequence: Let $a_{ik}$, i=1, . . . , m be the ranks of the spectral amplitude $A_{ik}$ in the kth sample. The phase angles $\phi_{ik}$ were replaced by the uniform scores $$\beta_{ik} = \frac{2 \cdot \pi \cdot r_{ik}}{n}.$$

The test statistics used for the modified q-sample uniform scores test is $$W^{1*} = \frac{2^2}{q^2 \cdot (q+1)^2} \cdot \frac{2}{m} \cdot \sum_{k=1}^{q} (C_k^{*2} + S_k^{*2}) \text{ with}$$

$$C_k^* = \sum_{i=1}^{m} a_{ik} \cdot \cos\beta_{ik}; \quad S_k^* = \sum_{i=1}^{m} a_{ik} \cdot \sin\beta_{ik} \text{ and}$$

$$\beta_{ik} = \frac{2 \cdot \pi \cdot r_{ik}}{n},$$

where
$r_{ik}$ are the ranks of the n phase angles (n=q×m), q is the number of samples
m is the sample size of the q samples and
$a_{ik}$ are the ranks of the n spectral amplitudes $A_{ik}$.

This already known test modification gains more information through inclusion of the spectral amplitudes than the "q-sample uniform scores test" of Mardia (1972) and it is still parameter-free because of the use of ranks instead of the real phase and amplitude values; however, working with ranks of phases and amplitudes instead of the actual values still means that the existing information is not used completely, which has the consequence that the test power is not optimal.

It is the object of the invention to create additional diverse modifications of the known "q-sample uniform scores test" in which the available information of phases or the phases together with the spectral amplitudes are fully used.

The following novel modifications of the known "q-sample uniform scores test" are proposed:

TEST MODIFICATION 2

Only the phase angles are used; however, in contrast to the known "q-sample uniform scores test" of Mardia, 1972, one does not work with the ranks but with the phase angles computed through Fourier transformation.

Let $\{x_{ik}; 1 \leq i \leq m, 1 \leq k \leq q\}$ be a collection of random variables (phase angles $\phi_{ik}$); q is the number of samples (spectral lines) with the sample size m (number of epochs), i.e. there are q×m=n phase angle values.

The test statistics used is $$W^{2*} = \frac{2}{m} \cdot \sum_{k=1}^{q} (C_k^2 + S_k^2) \text{ with}$$

$$C_k = \sum_{i=1}^{m} \cos\varphi_{ik};$$

$$S_k = \sum_{i=1}^{m} \sin\varphi_{ik}$$

where
q is the number of samples (number of includes spectral lines) and m is the sample size (number of epochs).

TEST MODIFICATION 3

Spectral amplitudes and phase angles are used in the known modification; however, the phase angles are not ranked while the ranks for the spectral amplitudes are still entered in the test. The spectral amplitudes $A_{ik}$ are ranked in a single sequence; Let $a_{ik}$, i=1, . . . m be the ranks of the spectral amplitudes $A_{ik}$ in the kth sample.

The test statistics used is $$W^{3*} = \frac{2^2}{q^2 \cdot (q+1)^2} \cdot \frac{2}{m} \cdot \sum_{k=1}^{q} (C_k^{*2} + S_k^{*2}) \text{ with}$$

$$C_k^* = \sum_{i=1}^{m} a_{ik} \cdot \cos\varphi_{ik};$$

$$S_k^* = \sum_{i=1}^{m} a_{ik} \cdot \sin\varphi_{ik}$$

where
q is the number of samples
m is the sample size of the q samples and
$a_{ik}$ are the ranks of the n spectral amplitudes $A_{ik}$
$\phi_{ik}$ are the phase angles.

TEST MODIFICATION 4

In this case, there are used directly (unranked) the values of the phase angles computed by means of Fourier transformation and the spectral amplitudes as well.

The test statistics used is $$W^{4*} = \frac{2^2}{q^2 \cdot (q+1)^2} \cdot \frac{2}{m} \cdot \sum_{k=1}^{q} (C_k^{*2} + S_k^{*2}) \text{ with}$$

$$C_k^* = \sum_{i=1}^{m} A_{ik} \cdot \cos\varphi_{ik};$$

$$S_k^* = \sum_{i=1}^{m} A_{ik} \cdot \sin\varphi_{ik}$$

where q is the number of samples m is the sample size of the q samples and $A_{ik}$ are the spectral amplitudes $\phi_{ik}$ are the phase angles.

A substantial problem in the use of the inventive test modification is the fact that the respective associated density function of the test values (probability density function) is unknown for the null hypothesis as a result of the performed modification. The critical test values necessary for the use of the test can therefore not be taken from the tables in the current literature (the test values are necessary for the decision of positive or negative test results).

The Monte Carlo simulation offers a known possibility for computation of the density function of the null hypothesis. A very large amount of pairs of random numbers are created hereby with a random number generator. A spectral amplitude and a phase angle are calculated from each pair of numbers and the statistical test is used thereafter. The distribution of the null hypothesis is calculated from the resulting large amount of test values. The searched critical test value can be read from the distribution.

However, the normal distribution of spectral amplitudes and phases accepted in the simulation cannot be assumed in the case of real spectral amplitudes and phase angles.

An element of the invention is therefore the following method for computation of the distribution of null hypothesis which takes into account the real distribution of spectral amplitudes and phase angles: Assumed is the presence of a great number (>100) of ASSR recordings whereby raw data of the derived electroencephalogram (EEG) has been continuously stored on the hard disk (approximately 200 epochs whereby the length of one epoch is approximately 1 second). As it is depicted in FIG. 1, the response is limited to a few spectral lines (the fundamental wave is 160 Hz and the higher harmonic is a multiple of 160 Hz). Since the spectral resolution is approximately 1 Hz at an epoch length of approximately 1 second, there are more than 150 spectral lines lying between two harmonics whereby said spectral lines contain only the noise resulting from the asynchronous EEG. If one applies the statistical test to these spectral lines, then one can obtain approximately 3,000,000 test values at 100 recordings of each 200 epochs (100×200×150). The distribution computed from these test values represent a very good estimate of the density function of the null hypothesis fitting the real data from which the searched critical test value can be read.

Figure 2:
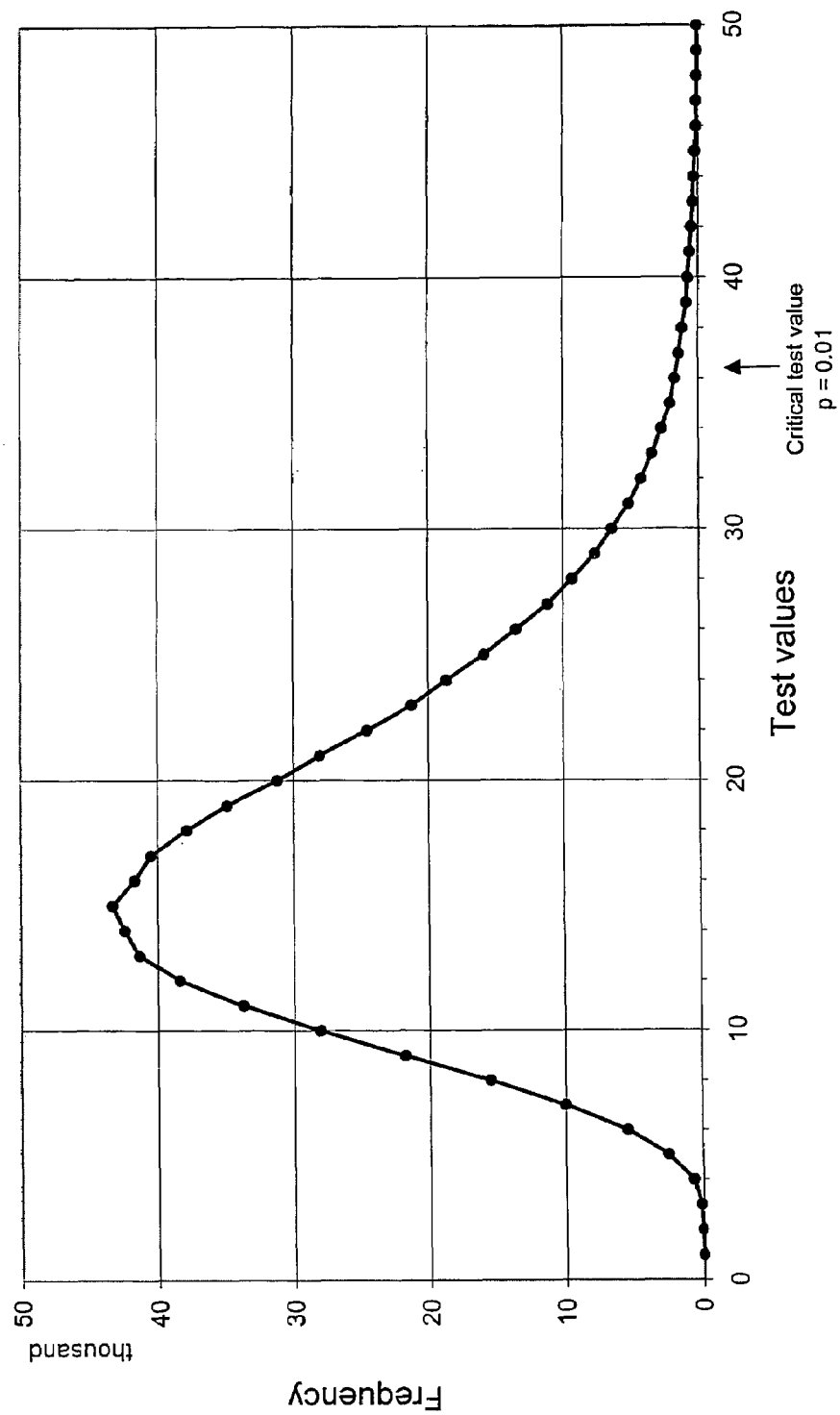

The density function of the null hypothesis calculated by means of the hereby described method is shown in FIG. 2 as an example for the Test Modification 1.

The use of the inventive solution has the following advantage:

While the known solution uses only partially the information contained in the spectrum because of the limitation of the ranks of the phase angles (q-sample uniform scores test) or the ranks of the phase angles together with the spectral amplitudes (Modification 1), more information (Modification 2 and 3) or the entire information contained in the spectrum (Modification 4) is used with the inventive modifications (Modification 2–4).

The result is a higher test power of the proposed modifications. A higher test power leads to the fact that the responses are detected more rapidly during hearing screening with a preset stimulus level and the time for screening is thereby shorter. A more exact objective threshold determination is made possible in an objective audible threshold determination as a result of the higher test power since the response verification becomes closer to the audible threshold of the patient himself.

The elimination of the distribution independence in the proposed modification is not a disadvantage since the appropriate distribution of the null hypothesis is determined by the data specified in the proposed method.

The invention claimed is:

1. A statistical testing method for the objective verification of auditory steady-state responses (ASSR) in the frequency domain by using a q-sample uniform scores test and comprising the steps of:

applying an acoustic signal to a test person, measuring the test person's electrical brain stem response signal to the acoustic signal, obtaining values of the phase angles by Fourier transforming the response signal, obtaining values of the spectral amplitudes by Fourier transforming the response signal, and applying the unranked values of phase angles and spectral amplitude directly in the q-sample uniform scores test.

* * * * *